(12) United States Patent
Brezinski

(10) Patent No.: US 9,604,072 B2
(45) Date of Patent: Mar. 28, 2017

(54) PORTABLE PHOTOTHERAPY DEVICE

(71) Applicant: Donna J. Brezinski, Winchester, MA (US)

(72) Inventor: Donna J. Brezinski, Winchester, MA (US)

(73) Assignee: LITTLE SPARROWS TECHNOLOGIES LLC, Winchester, MA (US)

(*) Notice: Subject to any disclaimer, the term of this patent is extended or adjusted under 35 U.S.C. 154(b) by 4 days.

(21) Appl. No.: 13/794,891

(22) Filed: Mar. 12, 2013

(65) Prior Publication Data

US 2014/0031906 A1 Jan. 30, 2014

Related U.S. Application Data

(60) Provisional application No. 61/676,137, filed on Jul. 26, 2012.

(51) Int. Cl.
*A61N 5/06* (2006.01)

(52) U.S. Cl.
CPC ............ *A61N 5/06* (2013.01); *A61N 5/0614* (2013.01); *A61N 5/0618* (2013.01);
(Continued)

(58) Field of Classification Search
CPC .............. A61N 5/06; A61N 5/0614; A61N 2005/0652; A61N 2005/0665;
(Continued)

(56) References Cited

U.S. PATENT DOCUMENTS 3,351,956 A * 11/1967 Thoner ............... A61H 33/06
392/326
3,875,596 A * 4/1975 Noda ................. A61H 33/06
4/527
(Continued)

FOREIGN PATENT DOCUMENTS

WO WO01/14012 A1 3/2001
WO WO2007/091188 A2 8/2007
(Continued)

OTHER PUBLICATIONS

International Search Report and Written Opinion, PCT/US2013/030484, dated Jul. 1, 2013, 13 pages.
(Continued)

*Primary Examiner* — William Thomson
*Assistant Examiner* — Victor Shapiro
(74) *Attorney, Agent, or Firm* — Yankwich & Associates, P.C.; Leon R. Yankwich; Michael R. Wesolowski

(57) ABSTRACT

Disclosed is a portable phototherapy device capable of emitting electromagnetic radiation of a wavelength and intensity sufficient to obtain a desired phototherapeutic effect to a subject, without being in direct physical contact with said subject. The device is portable, capable of being flattened, folded, rolled, compressed, or otherwise collapsed, to a size smaller than that of its operating size. The device may be of any size or shape, and may optionally comprise a frame support. The device may be powered by a variety of sources, including one or more batteries. The device may be configured to deliver electromagnetic radiation sufficient to obtain one or more of a variety of desired phototherapeutic effects.

20 Claims, 5 Drawing Sheets

(52) U.S. Cl.
CPC .......... *A61N 5/0621* (2013.01); *A61N 5/0624* (2013.01); *A61N 2005/0652* (2013.01); *A61N 2005/0662* (2013.01); *A61N 2005/0665* (2013.01)

(58) Field of Classification Search
CPC .......... A61N 5/0624; A61N 2005/0662; A61N 5/0621; A61N 5/0618
USPC .......... 320/102; 607/88, 90, 91; 362/249.04; 128/898; 315/224; 257/419
See application file for complete search history.

(56) References Cited

U.S. PATENT DOCUMENTS

| | | | |
|---|---|---|---|
| 3,877,437 A | 4/1975 | Maitan et al. | |
| 3,990,463 A * | 11/1976 | Norman | E04H 15/40 135/126 |
| 4,009,051 A * | 2/1977 | Kazis et al. | 320/102 |
| 4,955,876 A | 9/1990 | Millner | |
| 5,339,223 A | 8/1994 | Kremenchugsky | |
| 5,411,046 A * | 5/1995 | Wan | E04H 15/40 135/126 |
| 5,671,766 A * | 9/1997 | Williams | E04H 15/48 135/114 |
| 5,824,023 A * | 10/1998 | Anderson | 607/88 |
| 5,835,648 A | 11/1998 | Narciso et al. | |
| 6,045,575 A | 4/2000 | Rosen et al. | |
| 6,290,713 B1 * | 9/2001 | Russell | 607/88 |
| 6,596,016 B1 | 7/2003 | Vreman et al. | |
| 6,611,110 B1 * | 8/2003 | Fregoso | 315/224 |
| 6,645,230 B2 * | 11/2003 | Whitehurst | 607/88 |
| 6,676,655 B2 | 1/2004 | McDaniel | |
| 6,743,249 B1 * | 6/2004 | Alden | 607/88 |
| 6,811,563 B2 | 11/2004 | Savage et al. | |
| 6,872,220 B2 | 3/2005 | Williams et al. | |
| 6,955,684 B2 | 10/2005 | Savage et al. | |
| 7,094,378 B1 | 8/2006 | Goodrich et al. | |
| 7,131,990 B2 | 11/2006 | Bansal et al. | |
| 7,147,653 B2 | 12/2006 | Williams et al. | |
| 7,210,817 B2 * | 5/2007 | Lee et al. | 362/249.04 |
| 7,274,844 B2 | 9/2007 | Walt et al. | |
| 7,305,163 B2 | 12/2007 | Williams | |
| 7,306,620 B2 | 12/2007 | Cumbie | |
| 7,438,719 B2 | 10/2008 | Chung et al. | |
| 7,686,839 B2 | 3/2010 | Parker | |
| 7,824,435 B2 | 11/2010 | Samuel et al. | |
| 7,921,853 B2 * | 4/2011 | Fiset | 128/898 |
| 8,026,528 B2 | 9/2011 | Williams | |
| 8,048,136 B2 | 11/2011 | Chung et al. | |
| 8,069,857 B2 | 12/2011 | Chung et al. | |
| 8,202,307 B2 * | 6/2012 | Rodrigues et al. | 607/88 |
| 8,212,473 B2 | 7/2012 | Kaminska et al. | |
| 8,246,666 B2 | 8/2012 | Pressler et al. | |
| 8,512,386 B2 * | 8/2013 | Pipe et al. | 607/91 |
| 8,536,667 B2 * | 9/2013 | de Graff et al. | 257/419 |
| 2004/0138726 A1 | 7/2004 | Savage | |
| 2010/0106228 A1 * | 4/2010 | Gardner | 607/90 |
| 2011/0144727 A1 | 6/2011 | Benedict | |

FOREIGN PATENT DOCUMENTS

| | | |
|---|---|---|
| WO | WO 2011088121 A2 * | 7/2011 |
| WO | WO2012037355 A2 * | 3/2012 |

OTHER PUBLICATIONS

International Search Report for PCT/US2013/030484, Dated Mar. 1, 2014, 5 pages.
Botelho, Alyssa. 'Portable Jaundice Therapy Could Save Infants' Lives'. New Scientist 2013, vol. 20, No. 49 (Oct. 11, 2013) (http://www.newscientist.com/article/dn24396-portable-jaundice-therapy-could-save-infants-lives.html#. UlnOR_-8Ezw.gmail).

* cited by examiner

PORTABLE PHOTOTHERAPY DEVICE

CROSS-REFERENCE

This application claims the benefit of U.S. provisional patent application 61/676,137, filed 26 Jul. 2012, which is incorporated herein by reference in its entirety.

STATEMENT REGARDING FEDERALLY FUNDED RESEARCH

This invention was made with government support under grant R43 HD081745 awarded by the National Institutes of Health, and grant AID-OAA-F-14-00041 awarded by the United States Agency for International Development. The government has certain rights in the invention.

FIELD OF THE INVENTION

The invention is directed to a portable light-emitting device capable of delivering electromagnetic radiation (EMR) to a subject in an amount, and of a wavelength sufficient to achieve a desired effect in the subject.

BACKGROUND OF THE INVENTION

Exposure to electromagnetic radiation has a wide variety of effects on subjects. Typically referred to as "photo-" or "light-" treatment" or photo- or light-therapy", a wide variety of devices and "treatments" (exposure regimes, or dosing) have been developed. Such treatments range from imaging, to germicidal, to tissue repair or growth, to treatment of a variety of diseases and disorders. The desired phototherapeutic effect is typically a result of the exposure properties of the electromagnetic radiation; including, but not limited to, wavelength, intensity, duration, and frequency of exposure.

Examples of conditions for which phototherapy is considered useful for humans include, but are not limited to; tanning, wound repair, antiseptic treatment, acne, herpes, psoriasis, seasonal affective disorder (SAD), bulimia nervosa, sleep disorders, and skin cancer.

As a specific example, phototherapy has long been effective to treat jaundice (or hyperbilirubinemia). Jaundice is caused by an excess accumulation of bilirubin in the blood. Such a condition can quickly become debilitating and life-threatening if left untreated; especially in newborn infants (affecting 60% of all newborns). Exposing the newborn to certain types of (blue) light is effective to degrade (i.e., convert the compound to a more easily degradable isomer) excess blood bilirubin. Such phototherapy is typically only required for a few days (until the infant's liver is more able to bioprocess bilirubin).

Current phototherapy devices present several drawbacks, which hinder their efficacy and/or range of utility. These device drawbacks include their inability to control, and to direct the quality and quantity of light at the subject for treatment. Problems with undesirable and/or excessive temperature exposure are common. Many phototherapy devices are large, bulky, and unwieldy, requiring special facilities to maintain and to operate the phototherapy device.

All of these drawbacks are most pronounced when dealing with newborns during phototherapy treatment of jaundice: This class of subjects represents the most helpless, fragile, and sensitive of subjects in need of phototherapy. Conventional phototherapy treatment of newborns with jaundice involves placement of an infant in an isolette tank or incubator with direct use of high-powered lighting. In practice, these devices are sub-optimal in that they generate undesirable amount of heat, are bulky, obtrusive, and not portable. In addition, these devices are easily rendered ineffective as the subject moves around and outside of the area of proper exposure within the isolette, or as the devices are moved by caregivers in the process of tending to the subject, but are not then returned to their proper position.

Several developments have been made directed to wrap-around, vest-like, or other garment phototherapy devices. Other devices have been developed to position and to maintain the infant within a phototherapy device. Unfortunately these devices unduly restrain or confine the infant, resulting in an uncomfortable and stressful experience for the subject. In addition, such garment-type devices physically touch and cover the infant, resulting in reduced air ventilation and blood circulation, and further may compromise hygiene. In addition, such garment-type devices prevent any additional topical contact, treatment, monitoring, or caregiving access to the subject that may be needed or desired. Various phototherapy devices have been suggested and attempted (see, for example, U.S. Pat. Nos. 3,877,437; 4,955,876; 5,339,223; 5,400,425; 5,792,214; 5,835,648; 6,045,575; 6,290,713; 6,596,016; 6,811,563; 6,872,220; 6,955,684; 7,131,990; 7,274,844; 7,305,163; 7,306,620; 7,438,719; 7,686,839; 7,824,435; 8,026,528; 8,048,136; 8,069,857; 8,212,473; 8,246,666).

The present invention solves these problems and more. The present invention is an improvement over traditional phototherapy devices by being portable. The present invention is lightweight, capable of being flattened, folded, rolled, compressed, or otherwise collapsed, to a size smaller than that of its operating size. The present invention does not require special facilities for use; and allows for easy transport and shipment, as well as "in-home" or "field" application. The present invention is not limited or constrained by its power source, and can be powered by any of a number of sources, including line power, battery, and photovoltaics. The present invention allows for directed and uninterrupted phototherapy without unduly confining or restricting the subject. While being portable, the present invention is adaptable for fitted use over any pre-existing structure, framework, or device (e.g., infant incubator, crib, or bassinette). Unlike wraparound, or garment-type phototherapy devices, the present invention does not come into physical contact with the subject, but operates at a distance from the subject, thus avoiding any physical distress, harm, or discomfort to the subject, and allowing for proper ventilation and circulation. By operating at a distance from the subject the present invention also allows caregiver access to the subject without interrupting the phototherapy. The present invention avoids undesirable conditions such as excessive heat and or dehydration to the subject.

Finally, the present invention is easy, and inexpensive to manufacture, to transport, and to ship. The present invention requires no special facilities, equipment, power requirements, maintenance or training to assemble and to operate, thus making it particularly useful in areas of remote access, third world, and developing countries, where specific needs may be the greatest.

SUMMARY OF THE INVENTION

Provided herein is a novel portable phototherapy device that is inexpensive and easy to manufacture, to transport, to ship, and to use. The present invention has ultimate utility for end users in areas of their choosing or necessity.

The phototherapy device of the present invention comprises a light source, circuitry, a shell, and a power source. The light source is operably connected to the power source through the provided circuitry, and is attached to the shell. The light source is capable of transmitting light of sufficient intensity and wavelength to provide a desired phototherapeutic effect to a subject without being in direct physical contact with said subject.

The shell of the phototherapy device, as more fully disclosed and described herein, is not limited in its size, shape, or composition of matter. Importantly, the shell is capable of being flattened, folded, rolled, compressed, or otherwise collapsed, to a size that is less than the working space of the assembled and operational phototherapy device. In one aspect of the invention, the shell comprises a reflective surface. In another aspect of the invention, the shell is pliable. In another aspect of the invention, the shell comprises a cloth layer. In a further aspect of the invention the shell comprises a transparent plastic layer.

The light source of the phototherapy device, as more fully disclosed and described herein, is not limited in its composition, or operation, but refers to any source capable of emitting a detectable amount of electromagnetic radiation (EMR) of any range or specificity of wavelength. In one embodiment of the invention, the light comprises a plurality of light sources. In another embodiment of the invention, the plurality of light sources are distributed throughout the surface (e.g., an inner surface) of the shell of the phototherapy device. In another embodiment of the invention, the light source comprises light emitting diode (LED) devices. In one embodiment of the invention, the light source emits electromagnetic radiation in the range of (human) visible light. In another embodiment of the invention, the light source emits blue light. In another embodiment of the invention, the light source emits EMR of a wavelength(s) of a range of about 400 to about 550 nm.

The power source of the phototherapy device, as more fully disclosed and described herein, is not limited in its design or construction, but refers to any source capable of providing useable energy of a sufficient quality and quantity (e.g., voltage, wattage, amperage) to the light source of the phototherapy device such that the light source emits EMR. Typically, the power source is electrical in nature and may be provided as either Alternating current (AC) or Direct Current (DC), or some combination/transformation of both. In one embodiment of the invention, the power source is line power. In another embodiment of the invention, the power source is from a generator (e.g., biogas, thermo-electric). In another embodiment of the invention, the power source is from one or more batteries or fuel cells, which may be rechargeable or disposable. In one embodiment the battery is a 12 volt battery. In one aspect of the invention, the power source is photovoltaic in nature.

The circuitry of the phototherapy device, as more fully disclosed and described herein, is not limited in its design or construction, but refers to any operable means of transmitting useable energy from the power source to the light source. Typically, such circuitry utilizes wire capable of conducting electricity. In various embodiments of the invention, the circuitry may further comprise various controlling devices, including but not limited to switches, rheostats, potentiometers, transformers, voltage regulators, resistors, capacitors, sensors, and any number and variety of specialized integrated circuits.

The phototherapy device of the present invention is engineered to operate at a distance from the subject. Unlike other phototherapy devices, the present invention is designed to operate without being in direct physical contact with the subject of the phototherapy, thus avoiding physically constraining, compromising, or otherwise damaging situations for the subject due to physical contact, and allowing unhindered access to the subject of phototherapy. To achieve this end the phototherapy device of the present invention may be fashioned to be supported by some external and/or pre-existing structure or framework. For example, in the case of phototherapy for infants, the device may be shaped and fitted to be supported by an isolette, incubator, crib, or bassinette. Additional features of the phototherapy device may include snaps, fasteners, slots, or weights, as desirable, to keep the phototherapy device in place.

In one embodiment, the phototherapy device of the present invention further comprises a frame support. Such frame support is not limited in its composition, size, or shape, but, importantly, is semi-rigid to rigid enough to support the phototherapy shell. In one embodiment of the invention, the frame support comprises one of more flexible rods. In various embodiments of the present invention, the frame support may be attached to the shell. The attachment may be of a permanent nature or may be designed to be removable, i.e., attachable (or inserted) and detachable, using any number of attachment designs and devices known in the art.

Another aspect of the invention includes a method for treating a subject with the phototherapy device of the present invention. Such a method comprises positioning the phototherapy and a subject relative to each other such that the subject is capable of being exposed to the transmitting light of the phototherapy device, and exposing the subject to the transmitting light for a sufficient duration to achieve a desired phototherapeutic effect.

As more fully disclosed and described herein, the phototherapy device may be used to treat a variety subjects to achieve a desired phototherapeutic effect. By way of non-limiting embodiments, the phototherapy device of the present invention may be used to sterilize (e.g., using ultraviolet radiation) any number of substances (e.g., water) or surfaces (e.g., table or countertops). The phototherapy device of the present invention may be used to facilitate growth of plants. The phototherapy device of the present invention may be used for a variety of human applications. The phototherapy device of the present invention may be used for tanning of skin or to treat a variety of diseases and disorders, for example, seasonal affective disorder, acne, psoriasis, wound healing, and jaundice.

DETAILED DESCRIPTION OF THE INVENTION

Figure 1:
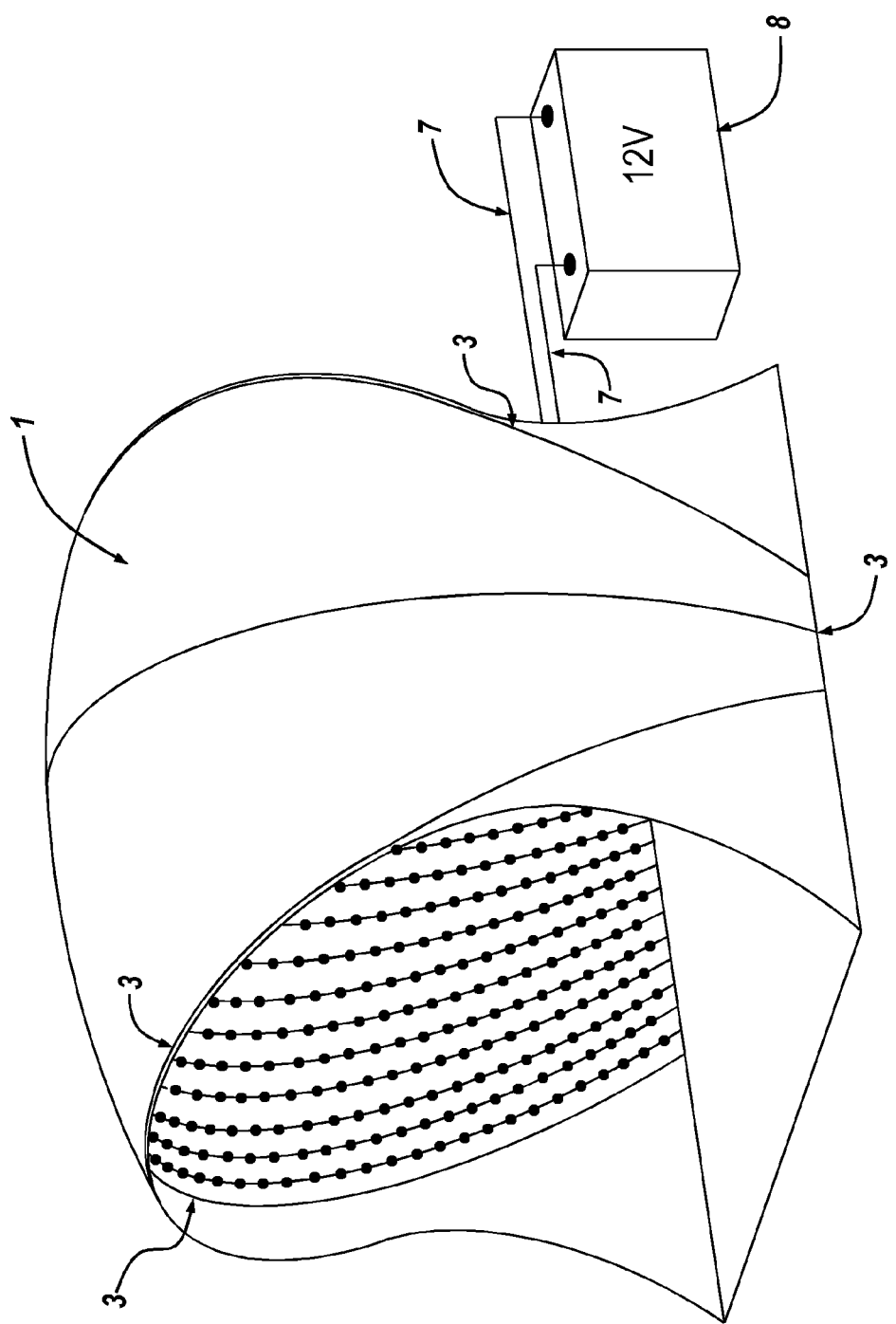
FIG. 1 is a perspective view of an assembled phototherapy device with attached battery power source. Identified within the FIG are; 1) the shell, 3) frame support, 7) circuitry, and 8) the power source.
Figure 2:
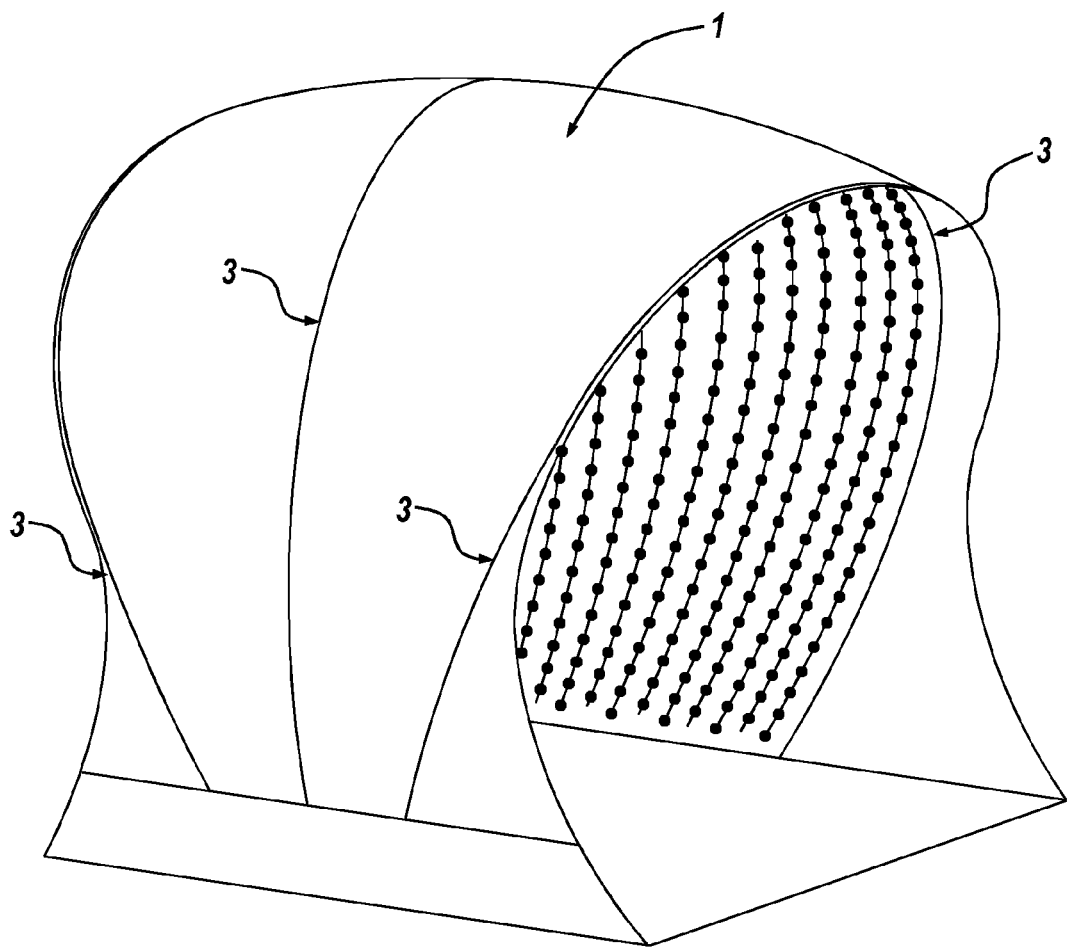
FIG. 2 is a reverse angle perspective of the assembled phototherapy device of FIG. 1 (power source out of view). Identified within the FIG are; 1) the shell, 3) frame support
Figure 3:
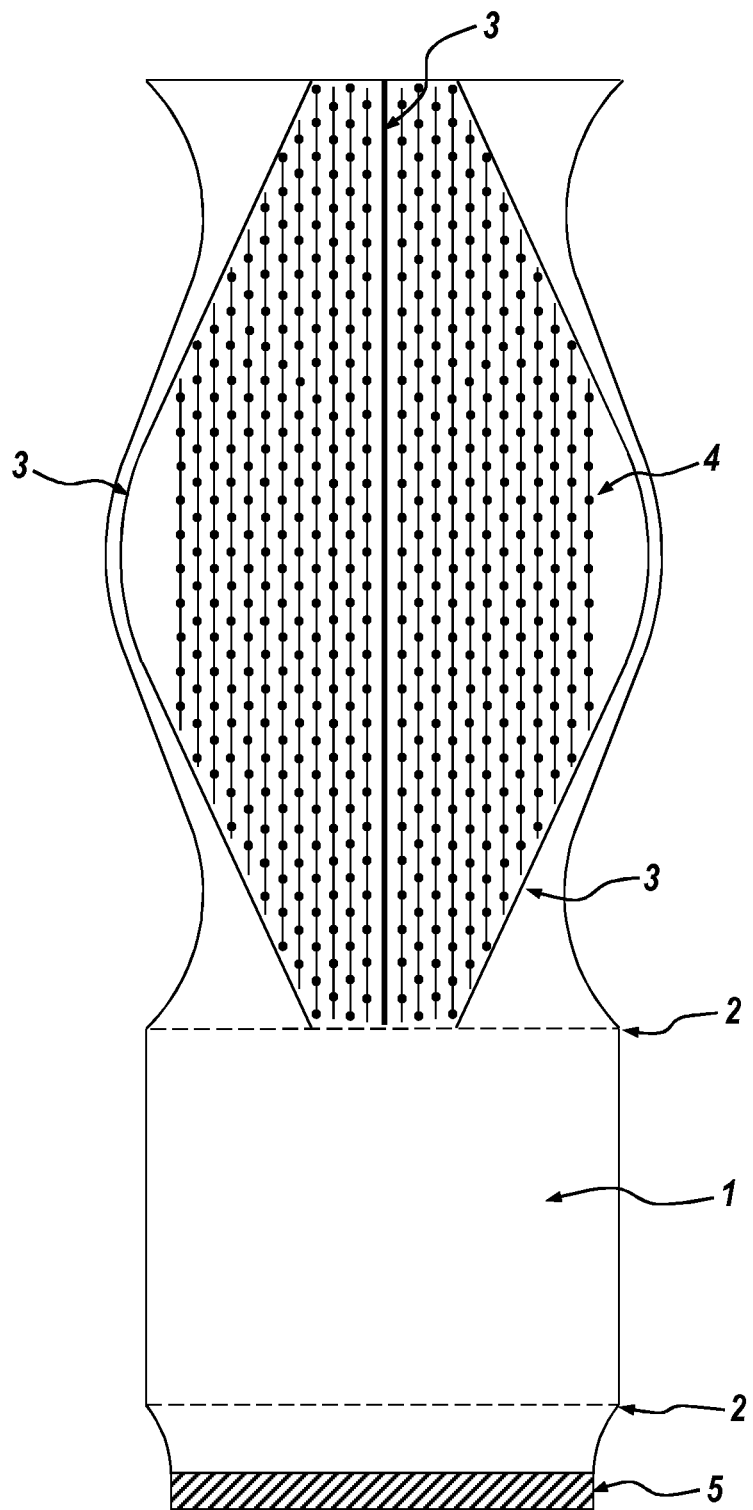
FIG. 3 is an interior perspective of an unassembled phototherapy device of FIGS. 1 and 2. Identified within the FIG are; 1) the shell, 3) frame support, 4) the light source.
Figure 4:
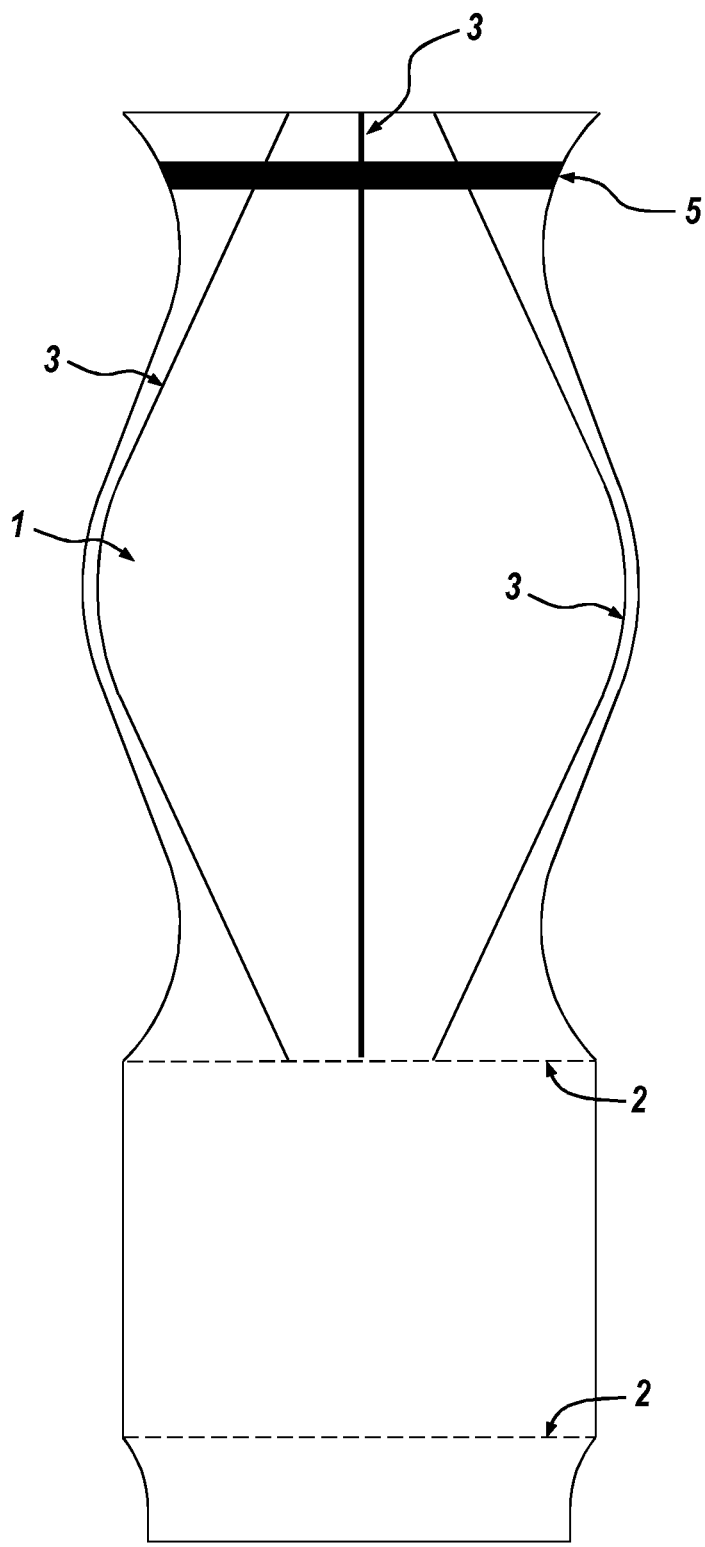
FIG. 4 is an exterior perspective of an unassembled phototherapy device of FIGS. 1-3. Identified within the FIG are; 1) the shell, 3) frame support.
Figure 5:
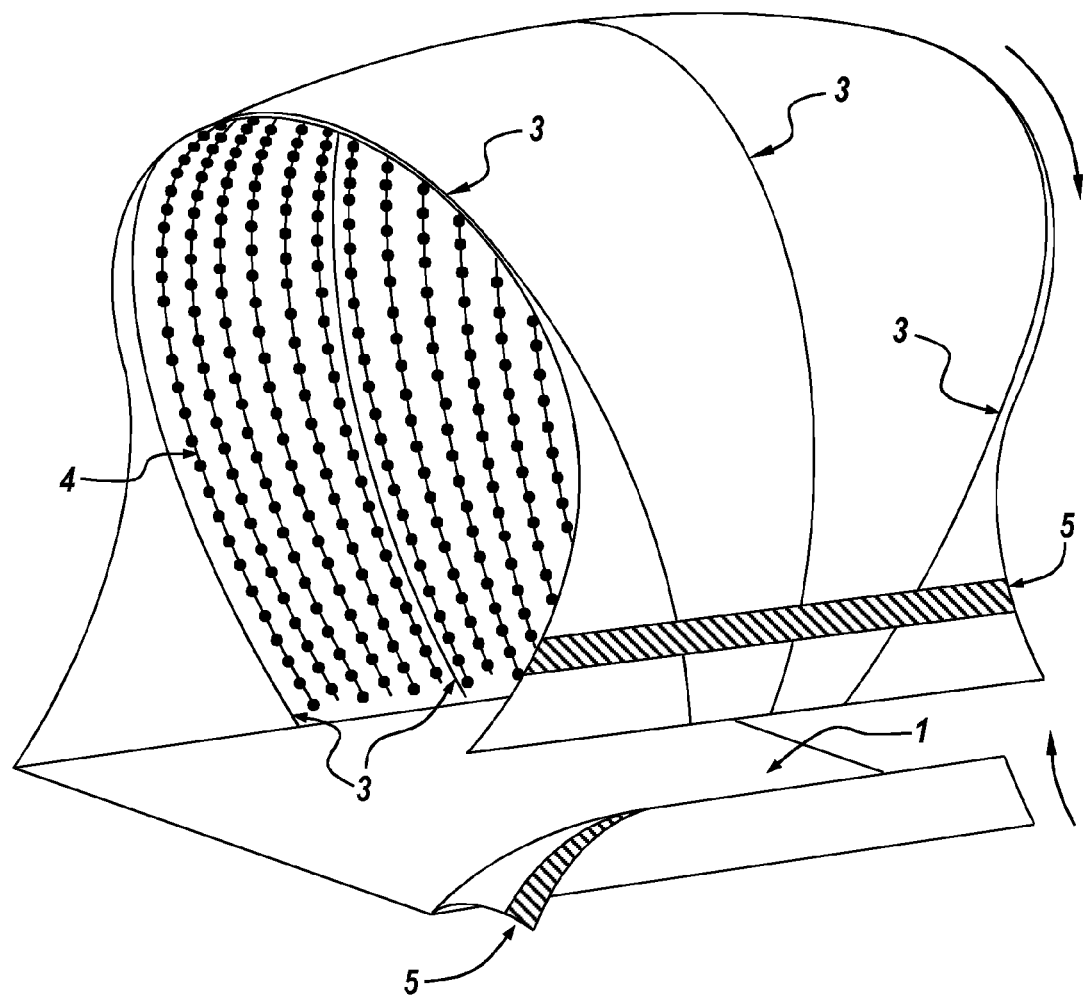
FIG. 5 is a perspective of a partially assembled phototherapy device of FIGS. 1-4. Identified within the FIG are; 1) the shell, 3) frame support, 4) the light source.

Provided herein is a portable light-emitting device capable of delivering electromagnetic radiation (EMR) to a subject in an amount, and of a wavelength sufficient to achieve a desired effect in the subject. The phototherapy device is inexpensive and easy to manufacture, to transport, to ship, and to use. The present invention has ultimate utility for end users in areas of their choosing or necessity.

The phototherapy device of the present invention comprises a light source, circuitry, a shell, and a power source. The light source is operably connected to the power source through the provided circuitry, and is attached to the shell. The light source is capable of transmitting light of sufficient intensity and wavelength to provide a desired phototherapeutic effect to a subject without being in direct physical contact with the subject. The phototherapy device of the present invention may be used for treating a subject. Such phototherapeutic treatment comprises positioning the phototherapy and a subject relative to each other such that the subject is capable of being exposed to the transmitting light of the phototherapy device, and exposing the subject to said transmitting light for a sufficient duration to achieve a desired phototherapeutic effect.

As used herein, the "subject" of phototherapeutic treatment is nonlimiting. The subject of phototherapy may be any nonliving surface or substance, or living sample. Importantly, the subject of phototherapy must be able to be in a position, relative to the phototherapy device of the present invention, such that the subject is exposed to the EMR emanating from the light source of the phototherapy device when the device is in operation. Nonlimiting examples of biological subjects of phototherapy include virus particles, single- and multi-cellular organisms including micro-organisms, fungi, plants, and animals (including humans), or any biological sample, organ, or tissue thereof.

Importantly the phototherapy device does not come in direct physical contact with the subject.

As used herein "direct physical contact" has the plain meaning as understood by a person of ordinary skill in the art. "Direct physical contact" refers to contact made by the shell and light source of the phototherapy device with the subject wherein, the device touches, lays, or rests upon the subject, or is wrapped around the subject, "Direct physical contact" does not refer to transmission, contact, or penetration of EMR emitted from the phototherapy device when operating. It is further understood that the phototherapy device may further be attached or connected to other components, which components may, themselves, be in direct physical contact with the subject of phototherapy. For example, it is envisioned that the phototherapy device may be integrated, connected, or attached to a floor, stage, platform, mat, or bed upon which the subject may be placed or lay. In addition, it is envisioned that the phototherapy device may be operably connected to components or devices, which may, themselves, be in direct physical contact with the subject, for example, for purposes of monitoring various states or conditions of the subject. It is understood that operation of the phototherapy device and the phototherapeutic effect is achieved by the transmission of EMR to the subject from a distance, without the shell or light source physically touching the subject.

As used herein, "attached" refers to any type or form of connection of one component to another. Attachment may be permanent or detachable. Nonlimiting example of permanent attachment include close integration of two components, such as being woven, interlaced, or glued together. By way of example, the shell of the phototherapy device may be woven together to a floor, staging or resting bed for the subject. The light source may be integrated, woven or glued into, or onto, the shell (see e.g., U.S. Pat. No. 7,274,844). Similarly, circuitry and frame support(s) may be integrated, woven or glued into, or onto, into the shell. Nonpermanent or detachable attachments are also envisioned forms of attachment. Such forms of attachment are meant to be assembled and disassembled, as needed or desired. Nonlimiting forms of detachable attachments include retaining channels or sheaths, loops, loops and hooks (e.g., VELCRO), slots, tabs, snaps, buttons, etc. For example, it is envisioned that portions of the shell of the phototherapy device may be detachably attached to itself or to a floor, stage, mat, or bed for assembly. It is also envisioned that the light source and frame support may be detachably attached to the shell using loops, sewn channels or sheaths, or VELCRO.

"Operatively connected" is a term commonly known and used by those of skill in the art, wherein the form of connection is defined functionally rather than structurally. Components are operatively connected when the components are so connected in such a fashion to allow the components to perform their understood or designated function. For example, the light source of the phototherapy device of the present invention is operatively connected to the power source in any such way that permits the transfer of energy from the power source to the light source such that the light source emits a detectable amount of EMR.

Phototherapeutic Effects and Applications

The phototherapy device of the present invention provides an efficient and effective means for applying electromagnetic radiation to subjects and substrates to achieve a desired phototherapeutic effect. Depending on the wavelength, intensity, and duration of EMR transmission to the subject a number of phototherapeutic effects may be obtained, ultimately due to its wide ranging effects at the atomic and molecular level. EMR exposure is known to, and used by, persons of skill in the art to effect a number of chemical changes and reactions. For example, EMR of a short wavelength (e.g., ultraviolet) may have a sterilization effect due to its potential DNA damaging effects on virus particles and organisms. As used herein, phototherapeutic effects may include imaging and heating effects. Phototherapy useful to effect plant growth is well known (e.g., grow lights). A number of phototherapeutic effects on animals, including humans are well-known, and more applications are continuing to be developed and discovered.

The phototherapy device of the present invention may be used for a variety of human applications. The phototherapy device of the present invention may be used for tanning of skin or to treat a variety of diseases and disorders. As nonlimiting examples, these phototherapeutic applications include treatment of circadian rhythm disorders (e.g., "jet lag"), seasonal affective disorder, non-seasonal depression and other psychiatric disorders, sleep disorders, acne, eczema, psoriasis, herpes, vitiligo, jaundice (hyperbilirubinemia), hair growth, blood circulation, sinus-related diseases and disorders, infections, wound healing (including surface cuts, and internal wounds such as broken bones or ligament damage), skin tuberculosis, cancer (e.g., cutaneous T-cell lymphoma), Parkinson's disease, and Alzheimer's disease. The desired characteristic of light (e.g., wavelength, intensity), dosing, and duration are selected by the practitioner, based upon the indication for treatment, the subject for treatment, and desired phototherapeutic effect.

The design and construction of the phototherapy device of the present invention is such that it is easily assembled (and disassembled) and operated by anyone with little or no technical expertise or training. Once assembled to its operational configuration, the method for use (treatment) of the phototherapy device comprises positioning the phototherapy device and subject, relative to each other such that the subject is capable of being exposed to the transmitting light of the phototherapy device, then exposing the subject to said transmitting light for a sufficient duration to achieve a desired phototherapeutic effect.

I. The Light Source

The light source of the phototherapy device is not limited in its composition, construction, or operation, but refers to any source capable of emitting a detectable amount of electromagnetic radiation (EMR) of any range or specificity of wavelength. As used herein, the terms "light", "light source", "phototherapy" and the like, are not limited in the wavelength of EMR emission, but encompass the full EMR spectrum, including what are commonly classified as; radio waves, microwaves, infrared light, visible light, ultraviolet light (e.g., UVA, UVB, UVC), X-rays, and gamma rays (static electricity and sound waves are not EMR). The light source may emit EMR of a single wavelength or any range of wavelengths. Similarly, the light source, and EMR emitted therefrom, is not limited in its intensity or duration of transmission. The light source may be active for continuous EMR transmission, intermittent EMR transmission, pulsed EMR transmission, or EMR transmission for a specified duration. Such intensity, frequency, and duration may be an intrinsic property of the light source, or may be further set or controlled by the circuitry of the phototherapy device.

The desired EMR transmission and light source are selected depending on the desired phototherapeutic effect the practitioner wishes to obtain. For example, UVA is known to be useful for phototherapy of psoriasis (in conjunction with photoactive agents). UVB is a DNA-damaging EMR, and is known to be useful for sterilization (e.g., germicidal), tanning, and the treatment for psoriasis. UVC is known to be useful for sterilization, including wound treatment. Light sources emitting EMR in the range of about 400 to about 550 nm are useful for treating jaundice. Light sources emitting EMR in the range of about 405 to about 420 nm are useful for treating Acne. Light sources emitting EMR in the range of about 465 to about 490 nm are useful for various circadian rhythm and sleep disorders. Light sources emitting EMR in the range of about 660 are useful for wound repair. Effective wavelengths cited herein may vary plus or minus 15%.

The light source of the present invention is not limited in number. The light source may comprise a single point source of light, or may comprise a plurality of light sources.

In one embodiment such plurality of light sources are distributed (evenly, uniform, non-uniform, or randomly) along a surface (e.g., inner surface), or portion of a surface of the shell. A variety of light sources are known and used in the art. Such light sources include, but are not limited to incandescent, fluorescent, laser, halogen, xenon, metal-halide, fiber optics, and light emitting diodes (LEDs; including organic light emitting diodes, OLEDs, and polymer light emitting diodes, PLEDs). Optionally, the light source may further comprise a filter to adjust or to narrow the wavelength of emitted EMR. The number of light strips required for a therapeutic level of light is determined by the total irradiance of the light source, as this may vary by manufacturer, the distance of the angle of light dispersion, the distance from the subject, and the reflectivity of the shell material.

In one embodiment, the light source is a plurality of LEDs. LEDs, and LED strings (or other arrays) are well known and commercially available (e.g., CREE, Inc., 4600 Silicon Drive, Durhanl, N.C. 27703; Nichia America Corporation, 3775 Hempland Road, Mountville, Pa. 17554). LEDs and LED arrays emit high intensity light at a low temperature, are inexpensive, lightweight, flexible, and may be selected based upon a wide variety of specific light wavelengths ("colors"); e.g., ~400 nm (violet light), ~475 nm (blue light), ~510 nm (green light), ~570 nm (yellow light), and ~650 nm (red light). LEDs that emit red light are useful for treating herpes. LEDs that emit white or yellow light are useful for treating SAD. LEDs that emit ultraviolet light are useful for treating psoriasis. LEDs that emit blue light are useful for treating jaundice, also known as hyperbilirubinemia. LEDS that emit blue light with a range of about 400 to about 550 nm are particularly useful. LEDS that emit blue light of about 450 to about 470 nm are preferred, as this is the range of light of peak absorption for bilirubin.

II. The Power Source

The power source of the phototherapy device is not limited in its design, construction, or output, but refers to any source capable of providing useable energy of a sufficient quality and quantity (e.g., voltage, wattage, amperage, resistance) to the light source of the phototherapy device such that the light source emits a detectable amount of EMR. Typically, the power source is electric in nature and may be provided as either Alternating Current (AC) or Direct Current (DC), or some combination/transformation of both.

In one aspect of the invention, the power source is line power. Line power, as is known in the art, generally refers to electricity distributed and provided as a service from a larger electricity generating source (e.g., "household power", "outlet electricity", "grid power", and the like). In another aspect of the invention, the power source maybe any of a number of generators, including but not limited to, a biogas generator or a thermo-electric generator. In another aspect of the invention, the power source is from one or more batteries or fuel cells. The battery power source may be rechargeable or disposable. Any of the wide array of batteries known in the art may be useful as a power source, including but not limited to dry cell, wet cell, alkaline, lithium, lithium-ion, lead-acid, and nickel-cadmium. In one embodiment the battery is a 12 volt battery. In one embodiment of the invention, the power source is photovoltaic in nature.

III. The Circuitry

The circuitry of the phototherapy device is not limited in its design or construction, but refers to any operable means of transmitting useable energy from the power source to the light source. Typically, such circuitry utilizes wire capable of conducting electricity.

In various embodiments of the invention, the circuitry may further comprise various regulating and controlling devices, including but not limited to switches, timers, rheostats, potentiometers, transformers, resistors, capacitors, sensors, data recorders, and any number and variety of specialized integrated circuits and components known in the art. In one embodiment, the circuitry further comprises over-voltage and/or short-circuit protection. The invention is not limited in design or placement of the various circuitry components. In some embodiments of the present invention, circuitry components may be positioned close to the light source (e.g., to monitor or control the light source). In other embodiments, various circuitry components may be positioned along a surface of the shell (e.g., to monitor or control the local environment of the phototherapy device). In other embodiments, various circuitry components may be positioned close to the power source (e.g., to improve the portability of the phototherapy device).

IV. The Shell ("Canopy")

For purposes of this disclosure, "shell" and "canopy" are used interchangeably. The shell of the phototherapy device is not limited in its size, shape, or composition of matter. Importantly, the shell is capable of being flattened, folded, rolled, compressed, or otherwise collapsed, to a size that is less than the working space of the assembled and operational phototherapy device. The shell, therefore, may be composed of two or more rigid panels that can articulate, or can otherwise be attached one to another such that they can be configured (e.g., "assembled") to form the structure of the phototherapy device, and can be alternatively configured (e.g., folded, or "disassembled") for easy transport or storage when not in use. In an alternative embodiment, the shell may be composed of a number of semi-rigid, pliable, or fabric materials, which material may be flattened, folded, rolled, compressed, or otherwise collapsed, to a size that is less than the working space of the assembled and operational phototherapy device. In one embodiment, the shell may be composed of any of a number of textiles, fabrics, or cloths known in the art. MYLAR is one fabric of particular utility in constructing the shell. One such example is "Grow tent reflective canvas" provided by Rogue Hydroponics (Hamden, Conn.).

The shell may possess any one or more physical characteristics that may provide additional benefit to the phototherapy device of the present invention, for example, to reduce, or to augment, environmental stimuli. In one embodiment, the shell may possess a reflective surface. Such a reflective surface, appropriately positioned relative to the light source serves to redirect transmission of EMR to the subject. The shell may be so constructed or fabricated such that the light source and/or circuitry is integrated into the shell (see, e.g., U.S. Pat. No. 7,274,844). The shell may be translucent, to permit light (or viewing) through the shell, or the shell may be opaque, to prevent light (or viewing) through the shell. The shell may further provide a surface (e.g., a transparent plastic layer), protective of staining, bodily fluids, cleaning solutions and the like. The shell may further provide sound deadening features to the phototherapy device.

The size and shape of the shell may be customized for any number of applications. For example, the shell may be fitted to conform to a pre-existing structure, such as an isolette, crib or bed (e.g., in the instance of phototherapy for infants). The shell may be fitted to conform to an aquarium or terrarium (e.g., in the instance of phototherapy for other animals or plants). The shell may be designed similar to, or modified from, any number of tent designs (e.g., in the instance of phototherapy for larger subjects, such as tanning devices for humans). The shell may further comprise any number and variety of retaining channels or sheaths, loops, clasps, hooks, buttons, holes, weights and the like to facilitate attachment of the phototherapy device to a pre-existing structure or otherwise immobilize the phototherapy device. The shell of the phototherapy device may take any of a variety of shapes, including but not limited to planar (panels), multi-faceted, conical, arched, tubular, or otherwise cylindrical or semi-cylindrical in shape.

V. The Frame Support

In one embodiment, the phototherapy device of the present invention further comprises a frame support. Such frame support is not limited in its composition, size or shape, but, importantly, is flexible, semi-rigid to rigid enough to support the phototherapy shell in a "free-standing" configuration. Similar to the shell, to maintain the portable feature of the phototherapy device, the frame support is capable of being flattened, folded, rolled, compressed, or otherwise collapsed, to a size that is less than the working space of the assembled and operational phototherapy device. In one embodiment, the frame support may be composed of two or more poles, rods, tubes, slats, springs, or the like that can articulate, or can otherwise be positioned one to another such that they can be configured (e.g., "assembled"), with the shell, to form the structure of the phototherapy device, and can be alternatively configured (e.g., folded, or "disassembled") for easy transport or storage when not in use. In an alternative embodiment, the frame support may be composed of one or more poles, rods, tubes, slats, springs, wire or the like that are capable of being flattened, folded, rolled, compressed, or otherwise collapsed, to a size that is less than the working space of the assembled and operational phototherapy device. As earlier discussed, the shell and frame support may be designed similar to, or modified from, any number of tent designs known in the art. In one aspect of the invention, the frame support comprises one of more flexible rods. In various embodiments of the present invention, the frame support may be attached to the shell. The attachment may be of a permanent nature or may be designed to be removable, i.e., attachable (or inserted) and detachable, using any number of attachment designs and devices known in the art. For example, non-conductive, extruded fiberglass rods (¼" or ⅜" diameter) are widely available, and may be cut to suitable lengths for any particular shell shape or design.

Unless otherwise noted, all of the technical terms used in this specification have the same meanings of those which are generally evident for persons in the technical field to which the invention is related. Methods and materials similar or equivalent to those described in this specification can be used in the construction, or operation, of the present invention. All publications and patent applications mentioned in this specification are herein incorporated by reference to the same extent as if each individual publication or patent application was specifically and individually indicated to be incorporated by reference.

The present invention is further illustrated by the following non-limiting example.

Example 1

Construction of the BILI-HUT

The non-limiting portable phototherapy device herein exemplified is specifically designed for the treatment of jaundice (hyperbilirubinemia) in newborn infants. This embodiment of the phototherapy device, the "BILI-HUT", is specifically designed for use in remote areas, where access to hospitals, clinics, and even line power is extremely limited.

As stated earlier, phototherapy devices to treat infant jaundice are difficult to use in low resource areas because they are rigid, heavy, and rely on line power. The invention claimed here solves this problem. This invention delivers therapeutic phototherapy by means of low energy, narrow wavelength, LED lighting. Energy requirement is further reduced by arranging the lights in an arch or curve and by the use of reflective materials. Problems of weight, rigidity and space are solved by use of a freestanding, flexible, collapsible tent, the BILI-HUT.

Current phototherapy devices rely on line power, are bulky, thus expensive to manufacture and distribute. This invention was powered by a rechargeable battery and can be used in areas without line power. It was made from lightweight material and can collapse for easier distribution to remote areas. It delivered light in arched pattern, more uniform light, with greater efficiency. Lower energy use enables operation from batteries charged by photovoltaic cells or intermittent line power. The lightweight, flexible, collapsible device was easily stored and transported, thus can be used in the field rather than exclusively in hospitals and clinics.

This specific embodiment of the BILI-HUT comprises the following elements and features:
1. flexible reflective material
2. fabric thread (natural or synthetic)
3. flexible support rods
4. flexible blue LED strip lighting
5. hook and loop tape
6. adhesive backing for lighting
7. wiring
8. 12 volt battery
9. switch
10. fabric binding Relationship Between the Components:

The flexible reflective material (1) was cut into a rectangular shape 68.5 inches×24 inches. This shape has regions corresponding to a floor, a canopy and a fold-over tab for securing the assembled device with hook and loop tape (5). The canopy region was configured with crescent shaped cut-outs at the far edges of each side of the canopy region. The lengths of the regions in sequence from the edge were as follows:

Canopy—43.5 inches;
Floor—20.5 inches;
Fold-over—4.5 inches.

When assembled, the device dimensions accommodated infants up to ~5 kg. The crescent cut-outs of the canopy section extended 12 inches along the far edge of each of the four ends of the canopy section along the long dimension. The deepest part of the crescent extended 4 inches from the edge. When assembled, these cut outs allowed a more comfortable position of the care provider's arms when attending to the patient.

The perimeter of the device was bound with fabric binding (10) using either adhesive (6) or thread (2). Three flexible support rods (3) were secured to the canopy region. These may be secured either to the interior or exterior of the canopy, and more support rods may be attached for additional stability. The manner for attaching support rods (3) was by threading them through sheaths sewn from the reflective material (1). They sheaths were of sufficient diameter and length to accommodate each flexible rod. A center sheath measuring 43.5 inches was attached to the canopy region, extending along the center of the long dimension of the canopy from the open edge of one side to the junction of the floor seam on the other. Two additional sheaths were attached to the outer side of the long dimension of the canopy region in a curved configuration such that the concave aspect of each curve faces the center sheath. The centers of each curve were attached as to be aligned with the center of each of the long edge of the canopy region. The ends of the sheaths were placed such that they were ~4 inches back from the fabric edge of the long dimension on each side of the canopy section. The length of the curved sheaths was ~44.5 inches. The sheaths were attached to the canopy by sewing, adhesive, or other mechanical application. The flexible support rods (3), cut to the length of the sheaths, were then threaded through the sheaths and the open ends were sewn shut.

Thread (2) was used to sew a linear seam in the reflective material (1) to facilitate linear bending along the junction of the floor and canopy on one side and the floor and the fold-over tab region on the other. A strip of one side of hook and loop tape (5) was attached along the edge of the fold-over region on the interior aspect of the material. The corresponding side of the tape was attached to the exterior aspect of the free end of the canopy section ~4 inches from the edge, a position aligning with the fold-over segment of tape. Flexible blue LED strip lighting (4) was attached using either adhesive (6) or thread (2) to the area of the reflective material (1) corresponding to the interior canopy, in the same orientation as the center flexible support rod. (3). The blue LED strip lighting (4) was connected in parallel circuitry with wiring (7) and attached to the canopy, directly to form an array of parallel strips on the interior. The light wiring (7) was connected to a switch (9) and 12 volt battery (8).

After procuring the component parts, the flexible reflective material was cut into the rectangular shape with crescent shaped cut outs as described. Two seams were sewn into the fabric at the boundaries of the section corresponding to the floor of the device. The perimeter of the fabric was then bound with fabric edging to prevent fraying. Three fabric sheaths of the lengths described were formed from the reflective material, then secured by adhesive to the center and sides of the canopy region in a manner to position the flexible rods as described. The flexible support rods were then threaded through the fabric sheaths and the open ends of the tubes are sewn shut. The flexible light strips were wired in parallel circuitry, and secured to the canopy with adhesive in an array that is parallel to the center support rod with equal numbers of strips placed symmetrically on either side of the center support. The total number of light strips required for a therapeutic level of light is determined by the total irradiance of the blue LED light source, the distance of the angle of light dispersion, the distance from the infant, and the reflectivity of the shell material. Here, 432 "Blue Ultra Bright LED's" on flexible strips (Inspired LED, Tempe, Ariz.) were arrayed, rectangularly, on a shell of "Grow tent reflective canvas" (Rogue Hydroponics, Hamden, Conn.), emitting a light intensity of 20.7 $\mu W/cm^2/nm$ over the surface of 20"×15" floor. The wiring was attached to an on-off type switch and connected to a solar chargeable 12 volt battery.

Creation of the flexible blue LED light array was achieved by grasping each end of the short edge of the reflective material and pulling such that the flexible rods became arched, the fold-over tab region at one edge extends beyond the opposite edge and is folded and secured by connecting hook and loop tape sections. This creates a but configuration with the light strips on the interior of the canopy positioned above the floor of the device. The device is switched on and a curved array of light illuminates the patient placed on the floor of the device.

Treatment for infants clinically diagnosed with jaundice comprises placing the infant inside the assembled BILI-HUT phototherapy device and turning the LED lights on. Actual phototherapy will vary depending upon the severity of the condition. Preferably, phototherapy is continuous until clinical signs of improvement are observed. Alternatively, conditions may dictate that a series of phototherapy treatments is warranted. Discontinuation of treatment may be based on decreased serum bilirubin levels (to clinically acceptable levels), or by physical clinical determination, such as lessening of yellow skin color. A typical course of treatment for an infant suffering from jaundice is three days of continuous phototherapy exposure.

The exemplary embodiments herein described are not intended to be exhaustive or to limit the scope of the invention to the precise forms disclosed. Those skilled in the art understand the inventive principles and concepts of the present invention disclosed and enabled by this specification, and appreciate that equivalents, alterations, and modifications of the elements and features of the present invention exist in the practice of this invention without departing from the spirit or scope thereof. For example, the various elements necessary to construct the phototherapy device of the present invention are defined by their necessary functional properties, and not limited, unless otherwise specified herein, by any particular composition of matter or structure. The terms used to describe such elements are intended to correspond, to any element capable of performing the defined necessary function of the described element. The metes and bounds of the invention are to be construed in accordance with the following claims.

I claim:

1. A portable phototherapy device adapted for the treatment of hyperbilirubinemia, comprising:
   (a) a floor section essentially rectangular in shape defined by a head end and a foot end and two sides, said floor being dimensioned so as to support the length of a reclining infant of up to about five kilograms, said floor having a fold-over tab attached along at least a portion of one side of the floor, the tab exhibiting one or more fasteners along its length;
   (b) a canopy section attached to said floor section along the side of the floor section opposite said fold-over tab, said canopy section extending from a proximal end attached to said floor section to a distal edge, said canopy section exhibiting one or more fasteners near its distal edge capable of mating with the corresponding fasteners on said fold-over tab to securely but reversibly join said distal edge of the canopy section to said fold-over tab, said canopy section being dimensioned such that joining said distal edge of the canopy section with the fold-over tab attached to said floor section forms an arcuate shell over said floor section, defining an assembled configuration having an inner surface facing said floor section and an outer surface;
   (c) a plurality of light sources affixed to the inner surface of said shell, said plurality of light sources being capable of emitting light of a wavelength of 400-550 nm;
   (d) an electrical power source;
   (e) circuitry operably connecting said power source to said plurality of light sources; and
   (f) one or more frame support elements affixed to said canopy section which are flexible yet rigid enough to support said canopy section in an arcuate shell configuration; wherein the inner surface of said shell comprises a reflective surface; and wherein said floor section, fold-over tab, and canopy sections are of a pliable material such that, when said fasteners are not fastened, said floor section, tab, and canopy section, together with said affixed plurality of light sources and frame support elements are, capable of being flattened or rolled or compressed to a disassembled size smaller than that of its operating size, and wherein, in the assembled configuration, said plurality of light sources is capable of transmitting light of sufficient intensity and wavelength to provide a desired phototherapeutic effect to an infant positioned on the floor section without said plurality of light sources of said device being in direct physical contact with said infant.

2. The portable phototherapy device of claim 1, wherein said floor section and said canopy section comprise a cloth layer.

3. The portable phototherapy device of claim 1, wherein said floor section is detachably attached to said canopy section.

4. The portable phototherapy device of claim 3, wherein said plurality of light sources are distributed throughout the inner surface of said shell.

5. The portable phototherapy device of claim 4, wherein said plurality of light sources are LED's.

6. The portable phototherapy device of claim 5, wherein said LED's are capable of emitting blue light.

7. The portable phototherapy device of claim 6, wherein said light source is capable of emitting light of a wavelength of about 450 nm to about 470 nm.

8. The portable phototherapy device of claim 1, wherein said power source is not line power.

9. The portable phototherapy device of claim 8, wherein said power source is a battery.

10. The portable phototherapy device of claim 9, wherein said battery is rechargeable.

11. The portable phototherapy device of claim 10, wherein said battery is a 12 volt battery.

12. The portable phototherapy device of claim 8, wherein power source is photovoltaic.

13. The portable phototherapy device of claim 1, wherein said circuitry comprises electrical wire.

14. The portable phototherapy device of claim 13, wherein said circuitry further comprises an on/off switch.

15. The portable phototherapy device of claim 1, wherein said frame support comprises one or more frame supports selected from the group consisting of poles, rods, tubes, slats, springs, and wire.

16. The portable phototherapy device of claim 15, wherein said frame support comprises one or more slats.

17. The portable phototherapy device of claim 15, wherein said frame support is detachably attached to said canopy section.

18. A method for treating a subject with a phototherapy device comprising:
   (a) providing a phototherapy device according to any of the phototherapy devices of claims 1 to 17,
   (b) positioning an infant in need of phototherapy on the floor of said device such that said infant is exposed to light emitting from said plurality of light sources, and
   (c) maintaining said exposure for a sufficient duration to achieve a desired phototherapeutic effect in said infant.

19. The portable phototherapy device of claim 15, wherein said frame support is non-detachably attached to said canopy section.

20. The portable phototherapy device of claim 15, wherein said frame support comprises one or more tubes, wherein said one or more tubes is capable of being flattened or compressed to a size that is less than the working space of the assembled and operational phototherapy device.

* * * * *